United States Patent
Dujmic

(10) Patent No.: US 9,980,697 B2
(45) Date of Patent: May 29, 2018

(54) REFERENCE DETECTOR FOR CORRECTING FLUCTUATIONS IN DOSE AND ENERGY OF X-RAY SOURCES

(71) Applicant: L-3 Communications Security & Detection Systems, Inc., Woburn, MA (US)

(72) Inventor: Denis Dujmic, Arlington, MA (US)

(73) Assignee: L-3 Communications Security & Detection Systems, Inc., Woburn, MA (US)

(*) Notice: Subject to any disclaimer, the term of this patent is extended or adjusted under 35 U.S.C. 154(b) by 307 days.

(21) Appl. No.: 14/980,284

(22) Filed: Dec. 28, 2015

(65) Prior Publication Data
US 2017/0184737 A1    Jun. 29, 2017

(51) Int. Cl.
*A61B 6/00* (2006.01)
*G01T 7/00* (2006.01)
(Continued)

(52) U.S. Cl.
CPC .............. *A61B 6/585* (2013.01); *G01T 7/005* (2013.01); *G01V 5/0016* (2013.01); *H05G 1/32* (2013.01); *G01N 23/06* (2013.01); *G01T 1/29* (2013.01)

(58) Field of Classification Search
CPC ........... A61B 6/00; A61B 6/42; A61B 6/4208; A61B 6/4233; A61B 6/4266; A61B 6/52; A61B 6/5294; A61B 6/58; A61B 6/582; A61B 6/585; A61B 2560/00; A61B 2560/02; A61B 2560/0223; A61B 2560/0228; A61B 2560/0233; A61B 2560/04; A61B 2560/046; A61B 2560/06; G01T 1/00; G01T 1/02; G01T 1/023; G01T 1/16; G01T 1/1603; G01T 1/185; G01T 1/20; G01T 1/2006; G01T 1/2018; G01T 1/24; G01T 1/242; G01T 1/244; G01T 1/34; G01T 1/36; G01T 1/361; G01T 1/362;
(Continued)

(56) References Cited

U.S. PATENT DOCUMENTS 4,811,373 A    3/1989    Stein
5,012,498 A *  4/1991    Cuzin .................... A61B 6/032
                                                250/370.15
(Continued)

FOREIGN PATENT DOCUMENTS

EP          0182529 A2    5/1986

OTHER PUBLICATIONS

Andreo, Pedro, et al. "Absorbed dose determination in external beam radiotherapy: an international code of practice for dosimetry based on standards of absorbed dose to water." International Atomic Energy Agency Technical Report Series 398 (Dec. 2000).
(Continued)

*Primary Examiner* — Anastasia Midkiff
(74) *Attorney, Agent, or Firm* — McCarter & English, LLP; David R. Burns

(57) ABSTRACT

Systems and methods presented herein provide corrections for fluctuations in dose or energy of radiation sources including x-ray radiation sources. The corrections can be applied to improve the quality of transmission radiography data or other radiation imagery or to facilitate feedback control of a radiation source to improve stability.

45 Claims, 13 Drawing Sheets

(51) Int. Cl.
*H05G 1/32* (2006.01)
*G01V 5/00* (2006.01)
*G01T 1/29* (2006.01)
*G01N 23/06* (2018.01)

(58) Field of Classification Search
CPC .......... G01T 1/365; G01T 1/366; G01T 7/00; G01T 7/005; H01L 25/00; H01L 25/03; H01L 25/04; H01L 25/041–25/043; H01L 25/065; H01L 25/0652; H01L 25/0655; H01L 25/0657; H01L 25/07; H01L 25/071–25/074; H01L 25/16; H01L 25/162; H01L 25/18; H01L 27/00; H01L 27/10; H01L 27/14; H01L 27/142; H01L 27/144; H01L 27/1446; H01L 27/146; H01L 27/148; H01L 31/00; H01L 31/02; H01L 31/0352; H01L 31/12; H01L 31/14; G01N 2223/00; G01N 2223/30; G01N 2223/303; G01N 2223/3037; G01N 2223/50; G01N 2223/501; G01N 2223/5015; G01N 2223/502; G01N 2223/503; G01N 2223/505; G01N 2223/5055; H05G 1/00; H05G 1/02; H05G 1/08; H05G 1/26; H05G 1/30; H05G 1/32; G01V 5/00; G01V 5/0008; G01V 5/0016; G01V 5/0041

See application file for complete search history.

(56) References Cited

U.S. PATENT DOCUMENTS

| | | | |
|---|---|---|---|
| 5,132,995 | A | 7/1992 | Stein |
| 5,841,832 | A | 11/1998 | Mazess et al. |
| 6,895,077 | B2 | 5/2005 | Karellas et al. |
| 8,488,736 | B2 | 7/2013 | Hoffman et al. |
| 2006/0078083 | A1 | 4/2006 | Nishide et al. |
| 2013/0327947 | A1* | 12/2013 | Ronda .................. G01T 1/1644 250/362 |
| 2014/0192954 | A1 | 7/2014 | Hanley |
| 2014/0341342 | A1* | 11/2014 | Desaute ................ G01N 23/04 378/53 |

OTHER PUBLICATIONS

International Search Report and Written Opinion for PCT/US2016/066329 dated Aug. 22, 2017, pp. 1-16.

\* cited by examiner

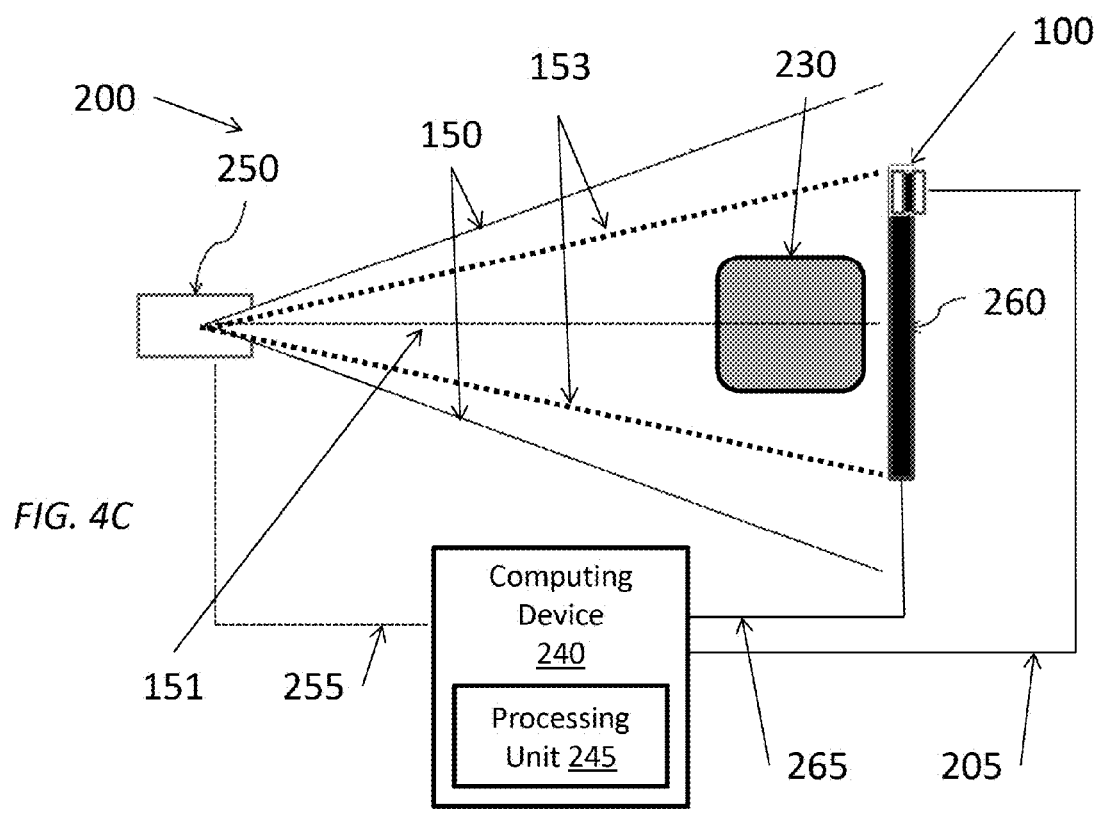
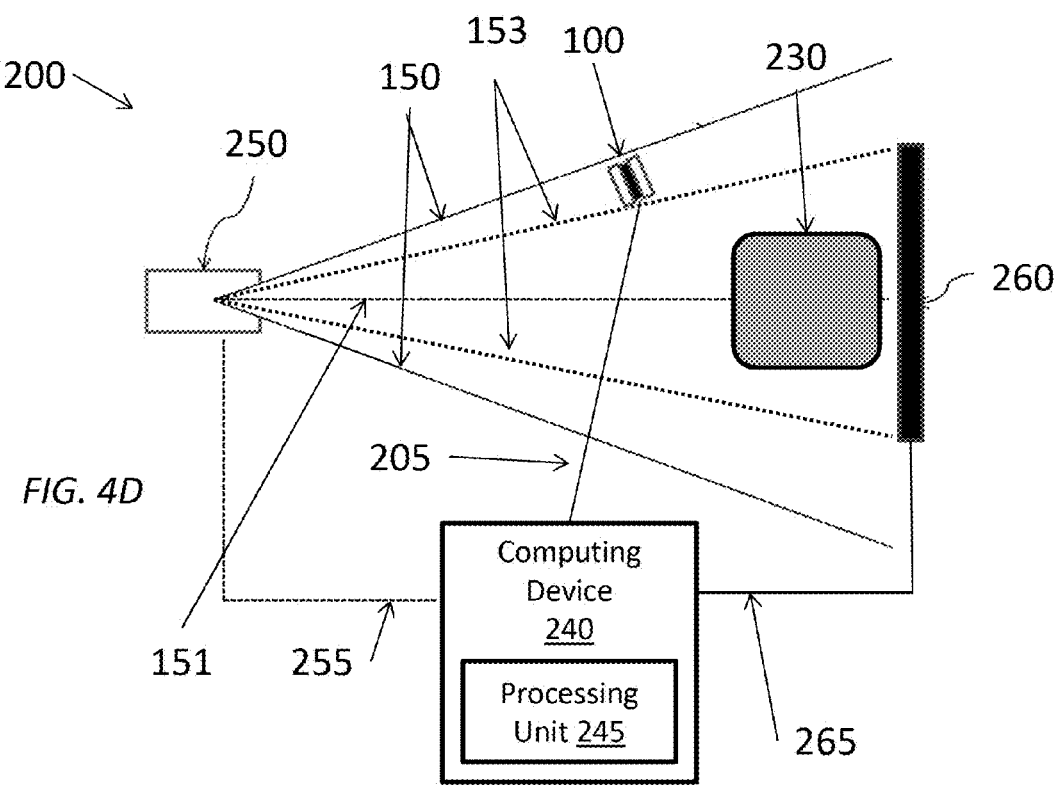

REFERENCE DETECTOR FOR CORRECTING FLUCTUATIONS IN DOSE AND ENERGY OF X-RAY SOURCES

BACKGROUND

Modern x-ray radiography systems measure x-ray attenuation through an object. Based on the properties of an x-ray source and detector in the system, the measured x-ray attenuation can provide information about the object's density, effective atomic number, or other properties. X-ray radiography systems can be used to detect suspicious items or contraband within cargo or baggage, for example, at an airport or seaport.

SUMMARY

Systems, devices, and methods are taught herein that enable the characterization of a high-energy x-ray source for dose and energy. Once the high-energy x-ray source is characterized for dose and energy, corrections to compensate for fluctuations in the dose and energy of an x-ray beam emitted by the high-energy x-ray source can be accomplished. In some embodiments, the disclosed systems, methods, and devices improve the quality of radiographic data indicative of x-ray radiation interacting with an object including density and atomic number data.

As taught herein, in some embodiments an x-ray imaging system is disclosed that includes a high-energy x-ray source, a detector array, a reference detector, and a processing unit. The high-energy x-ray source irradiates at least a portion of an object with a beam of x-ray radiation. The detector array detects object measurement data indicative of an interaction of x-rays with at least a portion of the object. The reference detector includes a plurality of detector elements stacked one behind the other in a stacking direction along an x-ray beam path to detect x-ray beam fluctuations in the high-energy x-ray source. The reference detector receives x-rays directly from the high-energy x-ray source. The processing unit has a central processing unit. The central processing unit is programmable to receive object measurement data from the detector array and measurements of an x-ray beam dose and the x-ray beam attenuation from the reference detector. The central processing unit is also programmable to determine a dose correction factor or energy correction factor using the measured x-ray beam dose and the measured x-ray beam attenuation from the reference detector. The central processing unit is also programmable to correct for x-ray beam fluctuations by applying the dose correction factor or energy correction factor to the object measurement data from the detector array.

As taught herein, in some embodiments a method of correcting for fluctuations in a beam of x-ray radiation from a high-energy x-ray beam source is disclosed. Performance of the method simultaneously measures an x-ray beam dose and the x-ray beam attenuation using a reference detector. The reference detector has a plurality of detector elements stacked one behind the other in a stacking direction along an x-ray beam path. The reference detector receives x-rays directly from the high-energy x-ray source. Performance of the method determines a dose correction factor or energy correction factor using the measured x-ray beam dose or the measured x-ray beam attenuation. Performance of the method corrects for the x-ray beam fluctuations by applying the dose correction factor, the energy correction factor, or both to measurement data representing density. Performance of the method corrects for the x-ray beam fluctuations by applying the dose correction factor and energy correction factor to measurement data representing effective atomic number. In some embodiments, performance of the method adjusts the high-energy x-ray beam source by applying the dose correction factor, energy correction factor, or both to the high-energy x-ray beam source.

As taught herein, in some embodiments a reference detector is disclosed that includes a plurality of detector elements. The plurality of detector elements are stacked one behind the other in a stacking direction along an x-ray beam path to detect x-ray beam fluctuations wherein a first detector element in the plurality of detector elements receives x-rays directly from a high-energy x-ray source. The stacking direction of the plurality of detector elements allows the reference detector to simultaneously detect the beam dose and the beam attenuation.

BRIEF DESCRIPTION OF THE DRAWINGS

The skilled artisan will understand that the drawings are primarily for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar or structurally similar elements).

The foregoing and other features and advantages provided by the present disclosure will be more fully understood from the following description of exemplary embodiments when read together with the accompanying drawings, in which:

FIGS. 4A-4D illustrate example reference detectors located at various positions in an example imaging system, according to embodiments of the present disclosure.

DETAILED DESCRIPTION

Below are more detailed descriptions of various concepts related to, and examples of, methodologies, computer readable media, apparatuses, and systems for characterization of fluctuations in the dose and energy of a high-energy x-ray source. Once the high-energy x-ray source's dose and energy fluctuations are characterized, corrections can be applied to compensate for fluctuations in the x-ray beam dose and energy. Advantageously, the characterization of a high-energy x-ray source for beam dose and energy fluctuations and the subsequent corrections for these fluctuations results in improvement in the quality of the radiographic image and measurement of the atomic number of an object under observation. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Systems, devices, and methods of the present disclosure enable correction of object measurement data obtained by transmission radiography systems to improve reconstructed image quality or to improve the ability to identify contraband, explosives, or other chemical or material components within objects. In particular, an x-ray imaging system is taught that that can obtain measurement data for at least a portion of an object. The system also measures the x-ray beam dose and x-ray beam attenuation using a reference detector. The system can correct the object measurement data for fluctuations of dose, energy, or both in a high-energy x-ray source using correction factors determined from the measured x-ray beam dose and attenuation. Methodologies are taught herein to enable correction for fluctuations of a high-energy x-ray source, and a device is disclosed including a stacked plurality of detector elements that simultaneously measures an x-ray beam dose and attenuation.

As used herein, "object measurement data" is data indicative of an interaction of x-ray radiation with at least a portion of an object and can include, but is not limited to, density and effective atomic number of the portion of the object.

As used herein, a "high-energy x-ray source" is an x-ray source that emits x-rays with an energy level of between 1 MeV and 20 MeV as characterized by the energy per unit mass deposited to a scanned object ('dose') and the energy spectrum ('energy').

Figure 1:
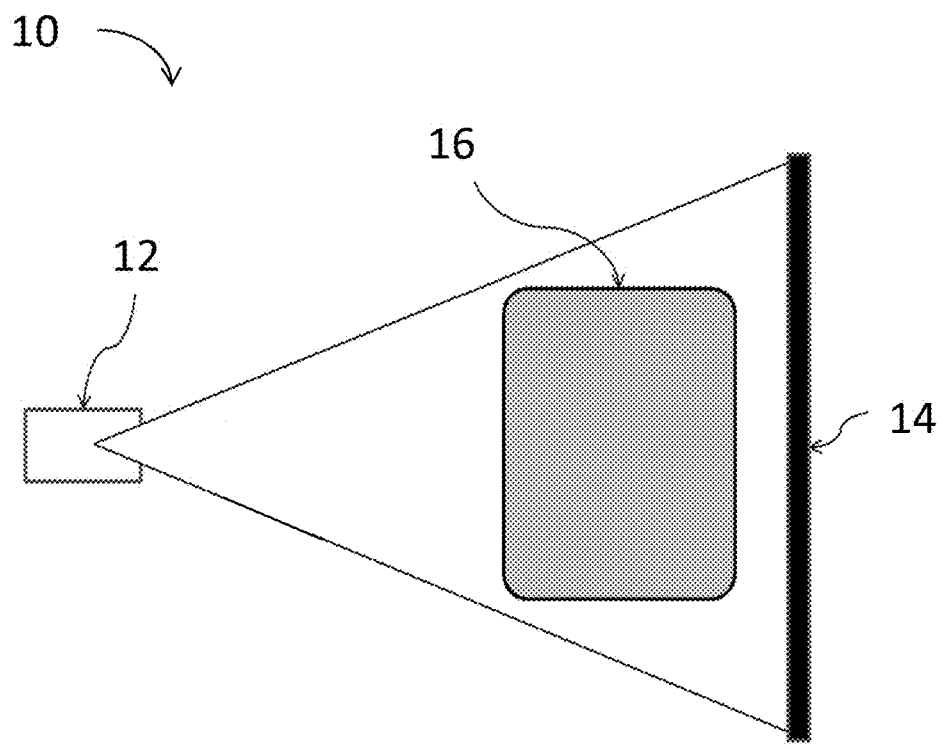
FIG. 1 illustrates an example prior art radiography system.

As illustrated in FIG. 1, a prior art x-ray radiography system 10 includes a high-energy x-ray source 12 and a detector array 14 that is used to measure x-ray radiation passing through an object 16. After the x-ray beam from high-energy x-ray source 12 passes through the object (having density ρ and thickness t), the detector signal (Y) at detector array 14 can be expressed as:

$$Y(t) = \int_0^{E_b} \Phi(E) \cdot e^{-\mu_T(E,Z)\rho t} \cdot \varepsilon(E) dE \quad (1)$$

where $E_b$ is the end-point of the x-ray energy distribution (Φ) that corresponds to the electron beam energy, ε is the detector response, and $\mu_T$ is the x-ray attenuation coefficient of the scanned material of the object 16. The x-ray attenuation coefficient ($\mu_T$) can be expressed as a sum of mass-normalized cross-sections from different sub-processes:

$$\mu_T(E,Z) = a_1(Z)\mu_1(E) + a_2(Z)\mu_2(E) + \ldots + a_n(Z)\mu_n(E) \quad (2)$$

where the coefficients $a_i$ (i=1, n) depend on the atomic number, and cross sections $\mu_i$ (i=1, . . . , n) depend on the energy of the x-ray. A radiographic image can be formed by using the measurements of the detector array 14 to provide a measure of the x-ray attenuation inside the material of the object 16. For scanning, using more than a single energy band of x-rays in the energy spectrum allows extraction of the effective atomic number of materials that make up the object 16. The stability of the high-energy x-ray source 12 can affect the accuracy of these measurements. The total error on the yield can be expressed as:

$$\sigma_Y^2 = \sigma_e^2 + g \cdot Y + r \cdot Y^2 \quad (3)$$

where $\sigma_e$ is the error due to the electronic noise of a detector in the detector array 14, and the g·Y term provides a measure of the variance due to x-ray counting statistics that depend linearly on the yield. Using an approximation based on proportionality between the detected signal and the number of x-rays (N) and the number of scintillation photons and the x-ray energy, the relative error on the detector yield can be expressed as $(\sigma_N/Y)^2 = 1/N + (\sigma_E/\langle E \rangle)^2/N$ so the variance on the detected yield scales as $\sigma_N^2 \propto N$. The $r \cdot Y^2$ term in Equation (3) represents the variance due to fluctuation in the beam dose or energy, and it scales as a square of the yield. The yield can be expressed based on the endpoint energy as follows: $Y = \gamma E_B^\delta$, such that $\sigma_Y/Y \propto \sigma_B/E_B$. In addition, the yield can be expressed as linearly dependent on fluctuations in the electron beam current in systems that generate x-rays using a high energy beam of electrons.

Figure 2:
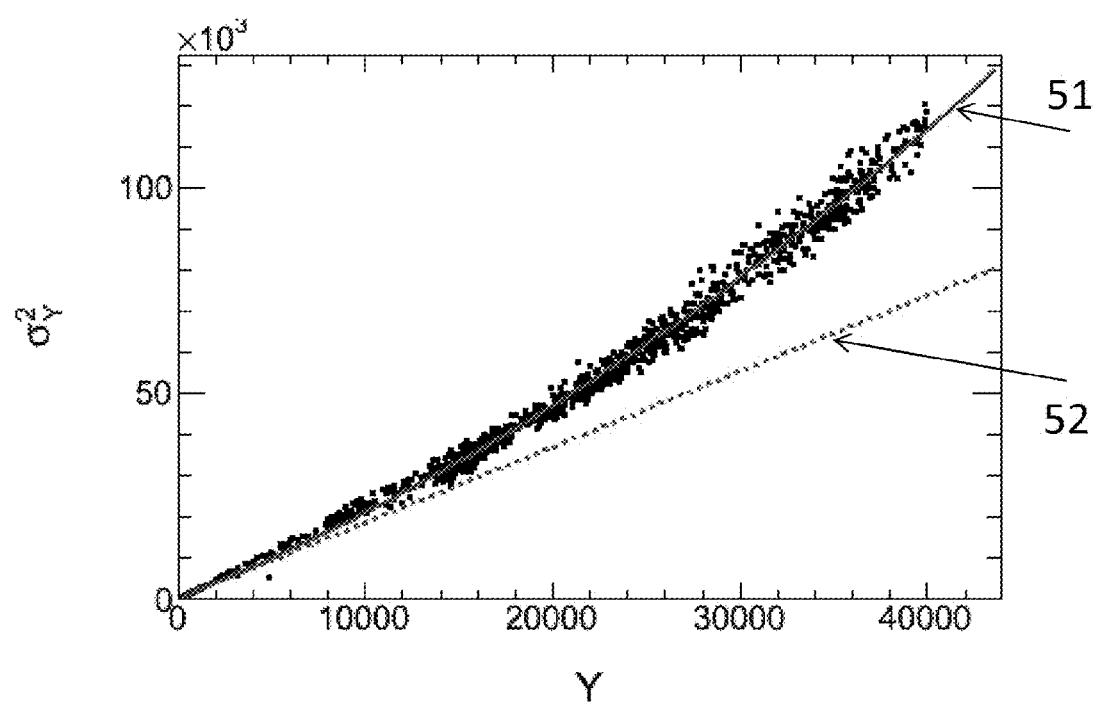
FIG. 2 illustrates an example plot of the dependence of beam variance on the yield of an example detector array, according to embodiments of the present disclosure.

FIG. 2 shows an example plot of the dependence of x-ray beam error $\sigma_Y^2$ on the yielded detector signal Y as discussed above in relation to Equation (3). A fit to the data (solid line 51) shows fluctuations of about 0.5% in the output beam dose or energy for an exemplary beam energy of 6 MeV. The dashed line 52 depicts the expected relationship under an assumption that the x-ray beam has no fluctuations, i.e., the final term in Equation (3) is zero. As shown in the plot of FIG. 2, in the case of large yield, e.g., for low object thickness where many x-rays penetrate the object and are detected, the beam dose fluctuations can dominate the yield error.

Energy and dose fluctuations often occur simultaneously. The dose fluctuations can impact the visual quality of radiographic images obtained using the prior art x-ray radiography system 10. The energy fluctuations of the high-energy x-ray source 12 can affect measurement of the x-ray attenuation in scanned objects 16. Variation on the order of a few percent in the attenuation measurement can inhibit the capability of the prior art x-ray radiography system 10 to discriminate between constituent materials of the object 16. As a non-limiting example, differences between aluminum and steel are on the order of about 1%.

The example reference detectors and systems, methodologies, computer readable media, and apparatuses including the reference detectors as taught herein, can be used to correct for both dose and energy variations in the prior art x-ray radiography system 10. Non-limiting example reference detectors are described hereinbelow in connection with FIGS. 3A through 4D.

Figure 3A:
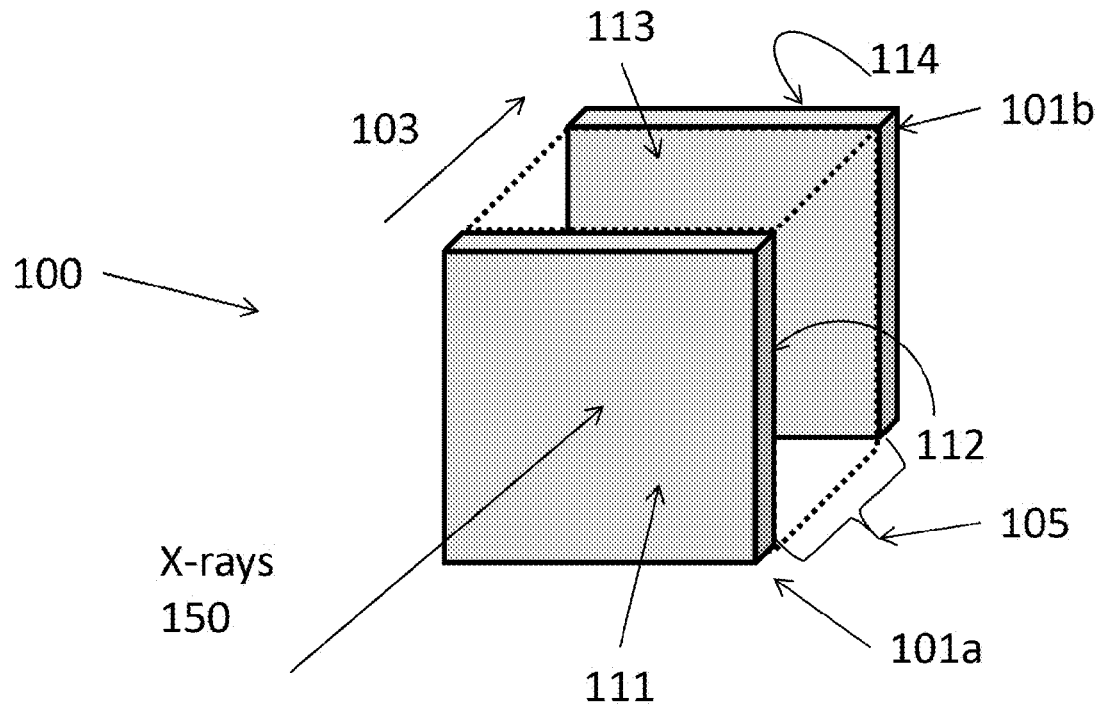
FIGS. 3A-3C illustrate example reference detectors, according to embodiments of the present disclosure.
Figure 3B:
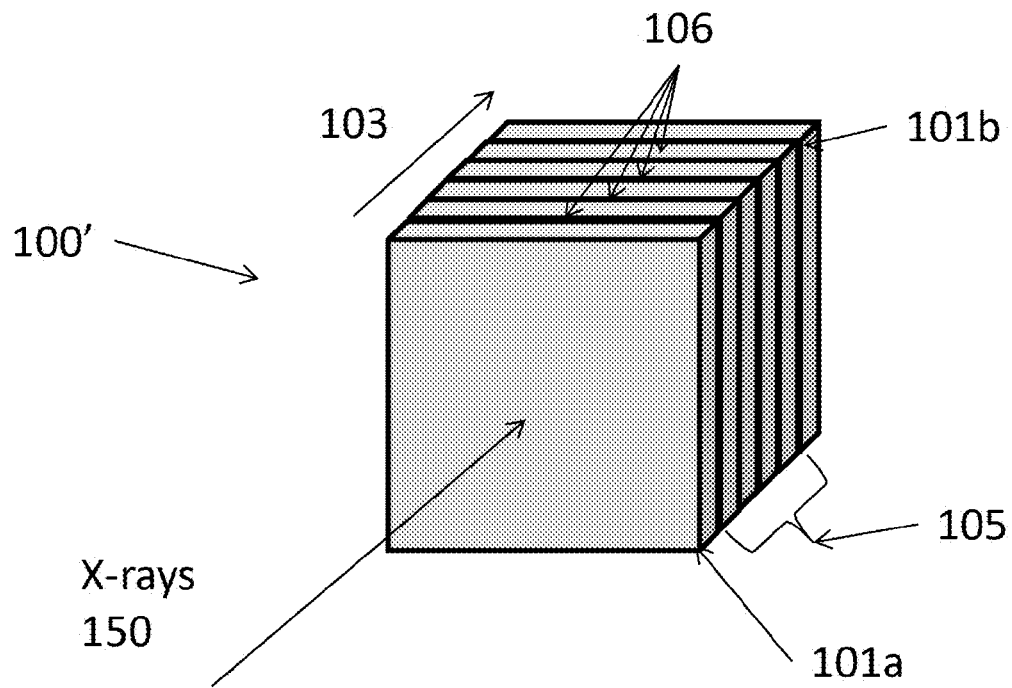
Figure 3C:
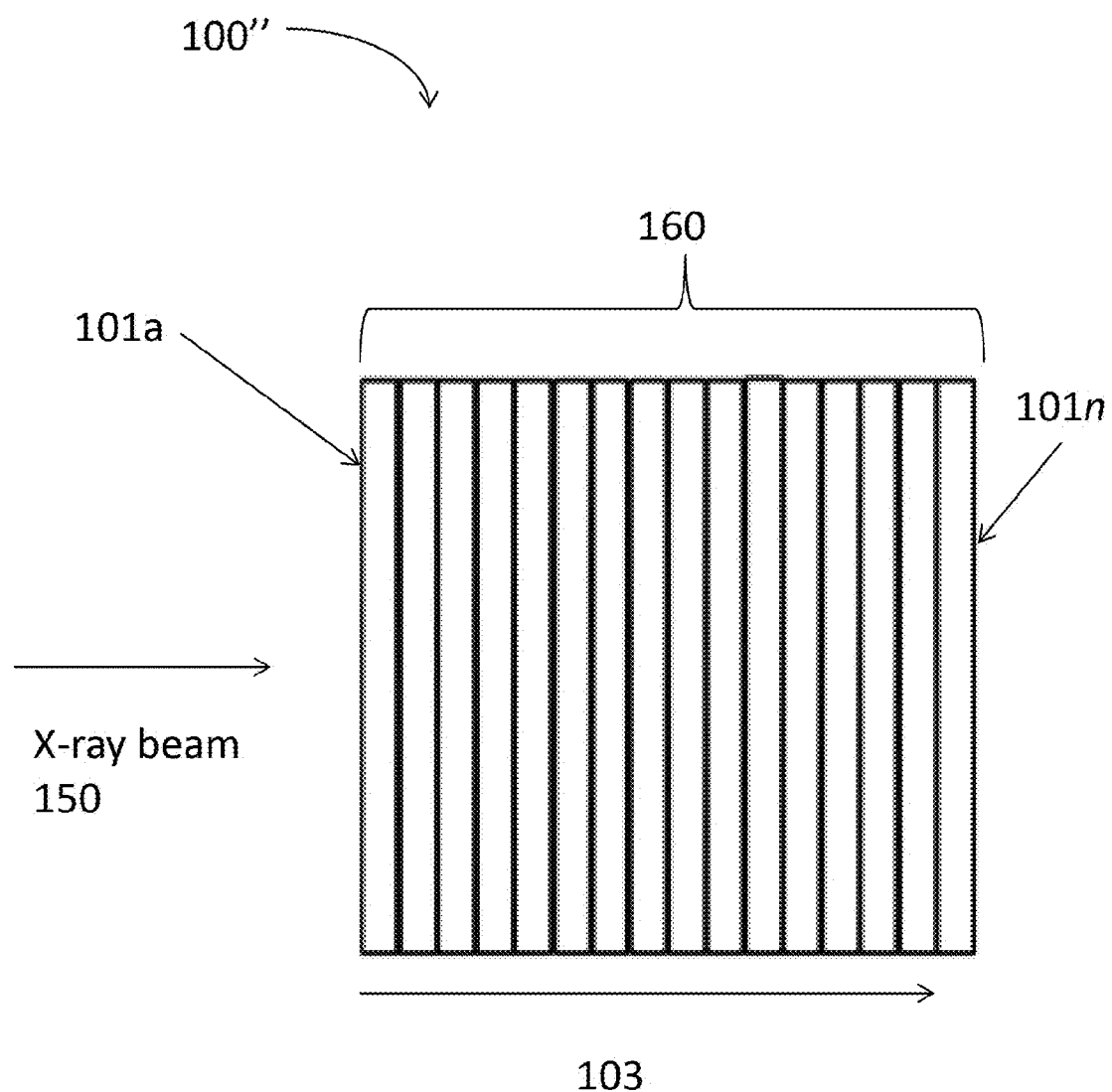

FIGS. 3A-3C illustrate example reference detectors according to various embodiments of the present disclosure.

The example reference detector 100 of FIG. 3A includes at least a first detector element 101a and a second detector element 101b disposed one behind the other along a stacking direction 103. The first detector element 101a and the second detector element 101b are configured to generate a first signal and a second signal, respectively, on exposure to a beam of x-ray radiation 150. Example reference detector 100 is configured such that the first detector element 101a and the second detector element 101b are spaced apart by a gap 105. In some embodiments, the gap 105 can be filled with one or more of air, detector elements 100, 100', 100", x-ray filters (described in greater detail below), or other materials or objects that do not attenuate the x-rays passing there through. In some embodiments, the first detector 101a and the second detector 101b may abut and touch one another. The placement of the first detector element 101a and the second detector element 101b one behind the other along the stacking direction 103 allows the reference detector 100 to detect both the dose and the attenuation of the beam of x-ray radiation 150.

The first detector element 101a can include a material that is sensitive to x-ray radiation. In some embodiments, the first detector element 101a can include a scintillator crystal such as, but not limited to, cadmium tungstate ($CdWO_4$; referred to herein as CWO), lead tungstate ($PbWO_4$), or cesium iodide (CsI). In alternative embodiments, the first detector element 101a can include an ionization chamber.

The first detector element 101a can have a first surface 111 that faces the beam of x-ray radiation 150 and a second surface 112 opposite to the first surface 111. In some embodiments, the first surface 111 can be positioned perpendicular to a central ray of the x-ray beam 150. In some embodiments, the first detector element 101a produces a signal on exposure to the beam of x-ray radiation 150.

The second detector element 101b can include a material that is sensitive to x-ray radiation. In some embodiments, the second detector element 101b can include a scintillator crystal such as, but not limited to, cadmium tungstate (CWO), lead tungstate ($PbWO_4$), or cesium iodide (CsI). In alternative embodiments, the second detector element 101b can include an ionization chamber.

The second detector element 101b can have a first surface 113 that faces the beam of x-ray radiation 150 and a second surface 114 opposite to the first surface 113. In some embodiments, the first surface 113 can be positioned perpendicular to the central ray of the x-ray beam 150. In some embodiments, the second detector element 101b can be formed from a different material or ionization chamber than the first detector element 101a. In some embodiments, the second detector element 101b can have a different conformation or lateral size than the first detector element 101a. In some embodiments, the second detector element 101b produces a signal on exposure to portions of the beam of x-ray radiation 150 that pass through the first detector element 101a.

FIG. 3B illustrates another example reference detector 100' that includes at least the first detector element 101a and the second detector element 101b disposed one behind the other along the stacking direction 103. As shown in FIG. 3B, the gap 105 can include one or more spacing elements 106. In some embodiments, the spacing elements 106 can be one or more x-ray filters formed from lead, tungsten, a combination thereof, or any other suitable high-Z material. The placement of the first detector element 101a and the second detector element 101b one behind the other along the stacking direction 103 allows the reference detector 100' to detect both the dose and the attenuation of the beam of x-ray radiation 150. The spacing elements 106 can also include other materials such as plastics, foams, that do not attenuate the x-rays passing there through or other materials with a known x-ray attenuation value.

In various example embodiments, the size of the gap 105 between detector elements can be set to any length that meets an application-specific requirement. In some embodiments, the gap 105 can include the same type of spacing element 106, for example, all reference detectors or a combination of spacing elements 106, for example, a combination of reference detectors and x-ray filters. In some embodiments the spacing elements abut adjacent elements. In some embodiments, one or more air gaps are included between the spacing elements 106. In an embodiment where characterized x-ray filters are used, the x-ray beam 150 can be attenuated by a known amount as it passes through the spacing elements 106. In some embodiments, the x-ray filter can be selected to have a high attenuation value to create a more compact reference detector 100'. X-ray filters can be useful in embodiments where the detector elements 101a, 101b are gaseous ionization chambers. Gaseous ionization chambers can be relatively inexpensive and long-lasting although they can have a small x-ray absorption cross-section. The addition of high attenuation value x-ray filters as spacing elements 106 can cause the reference detector 100 to be less dependent upon attenuation in the detector elements themselves.

In example reference detectors 100 and 100', the second detector element 101b is disposed behind the first detector element 101a along the stacking direction 103 such that the first surface 113 of the second detector element 101b faces the second surface 112 of the first detector element 101a. In an exemplary embodiment, the stacking direction 103 is parallel to a central ray of the x-ray beam 150. In some embodiments, the stacking direction 103 can be perpendicular to the first surface 111 or the second surface 112 of the first detector element 101a or the first surface 113 or the second surface 114 of the second detector element 101b. Alignment of the first detector element 101a and the second detector element 101b one behind the other along the stacking direction 103 allows the simultaneous detection of the dose and the attenuation of the x-ray beam 150 by the reference detector 100, 100'. In some embodiments, a signal from the second detector element 101b can be read out separately from a signal from the first detector element 101a. The detected beam dose can be correlated to a first signal from the first detector element 101a, a second signal from the second detector element 101b, or a sum of the first signal and the second signal. The detected beam attenuation can be correlated to an energy level of the beam of x-ray radiation 150.

In some embodiments of example reference detectors 100, 100', the second surface 112 of the first detector element 101a abuts the first surface 113 of the second detector 101b, such that there is no gap 105.

FIG. 3C depicts a side view of an example reference detector 100". The example reference detector 100" can include a plurality of detector elements 160. The plurality of detector elements 160 can include individual detector elements 101a, 101b, . . . , 101n as discussed above. Each individual detector element 101a-101n of the plurality of detector elements 160 can provide measurements of the x-ray beam 150 to improve overall reliability and signal-to-noise ratio while also providing additional data points for regression analysis. In some embodiments, no gap exists between any of the plurality of detector elements 160.

The example reference detectors according to various embodiments of the present disclosure, including any of reference detectors 100, 100' or 100", can be used to measure both the beam dose and the beam energy of the x-ray radiation. For ease of the discussion below, reference detector 100 will be referred to hereinafter although the below description is equally applicable to the reference detector 100' and the reference detector 100".

The reference detector 100 can be positioned so that it is exposed to a portion of the beam of x-ray radiation 150 that does not interact with an object being scanned, and the reference detector 100 can have direct access to the beam output. That is, the reference detector 100 is placed in the system so that an unobstructed, direct line of sight between the output of the high-energy x-ray source and the reference detector 100 is created. The example reference detector 100 can be disposed relative to the x-ray beam such that at least a portion of the first detector element 101a measures the direct x-ray beam dose and at least a portion of another detector element (such as detector elements 101b-101n) measures the dose after attenuation through a known set of materials (including detector element 101a). In some embodiments, the energy spectrum of the x-ray beam 150 changes as the beam passes through detector elements 101a-101n or spacing elements 106, i.e., as the beam is attenuated. In such embodiments, each detector element 101a-101n of the reference detector 100 can be exposed to a different energy spectrum.

While example systems, methodologies, apparatuses, and computer readable media in connection with FIGS. 4A through 11 may be described and illustrated relative to a reference detector 100, it is to be understood that either of reference detector 100' or 100" could be used in place of reference detector 100.

In many x-ray radiography systems, the high-energy x-ray source 250 can exhibit fluctuations in dose or energy from pulse-to-pulse. This instability often arises due to the method of producing high-energy x-rays. In high-energy x-ray sources that use a linear electron accelerator, for example, discrete pulses of high-energy electrons are directed onto a target that emits x-rays when struck by high-energy electrons. Subtle variations in the number of electrons or the accelerating gradient can produce fluctuations in the resulting pulse of x-rays. Because image reconstruction and material classification rely on measurement of x-ray beams that have been attenuated by passage through at least a portion of an object, fluctuations in the energy or dose of x-rays in the x-ray beam between pulses can degrade the quality of the object measurement data and, hence, the reconstructed image or material classification of the object. Systems, devices, and methods taught herein can correct for fluctuations in dose and energy of the x-ray beam by providing measurements of the dose and energy of the x-ray beam to determine correction factors that can be applied to object measurement data. This can be accomplished on a pulse-to-pulse basis.

During operation of any of the embodiments of the present disclosure, the reference detector 100 can be positioned relative to the high-energy x-ray source 250 such that the x-ray beam 150 is directed from one side and passes through the stacked detector elements 101a . . . 101n of the reference detector 100. This allows measurement of the beam dose and evaluation of the beam energy by measuring the yield across elements. Attenuation through the reference detector material is recorded as the decreasing yield through the stacked detector elements 101a . . . 101n of the reference detector 100.

FIGS. 4A-4D illustrate various embodiments of an example imaging system that include the reference detector 100 according to the principles described in this disclosure.

The example imaging system 200 can include a high-energy x-ray source 250, a detector array 260, a computing device 240 including a processing unit 245, and the reference detector 100. The example imaging system 200 can be used to obtain measurement data indicative of an interaction of x-rays with at least a portion of an object 230. Output from the reference detector 100 can be used to determine a dose correction factor, an energy correction factor, or both based on measurements of an x-ray beam dose and the x-ray beam attenuation, respectively, detected by the reference detector 100. The imaging system 200 can correct object measurement data using the dose correction factor, energy correction factor, or both.

The high-energy x-ray source 250 can be configured to emit a beam of x-ray radiation to irradiate at least a portion of the object 230. The detector array 260 can be configured to detect measurement data indicative of an interaction of the x-ray radiation with the portion of the object 230. As a non-limiting example, the detector array 260 can detect attenuated radiation that has passed through a portion of the object 230. The high-energy x-ray source 250 of some embodiments can include a high-energy electron beam and an extended target or array of targets. For example, the high-energy x-ray source 250 can include a linear electron accelerator (linac). In some embodiments, example imaging systems as taught herein can include more than one source 250 or more than one detector array 260.

Each pulse of x-rays from the high-energy x-ray source 250 can be characterized by its energy and dose. Values of x-ray energy and x-ray dose can fluctuate from pulse to pulse. Fluctuations in x-ray energy and dose for x-rays emitted by the high-energy x-ray source 250 can depend on the output x-ray energy. For example, high-energy x-ray sources 250 can have greater fluctuations in the x-ray energy and dose than low-energy x-ray sources. In some embodiments, the high-energy x-ray source 250 can emit x-rays with an energy level of at least 1 mega-electronvolt (MeV).

The reference detector 100 of the imaging system 200 can include a plurality of detector elements stacked one behind the other in a stacking direction along an x-ray beam path to simultaneously detect x-ray beam dose and energy fluctuations in the high-energy x-ray source. In some embodiments, the reference detector 100 is as described above with reference to any of FIGS. 3A-3C. The reference detector 100 may be placed in multiple different positions with respect to the source 250, object 230, and detector array 260 as long as there is an unobstructed line of sight between the output of the source 250 and the reference detector 100. In exemplary embodiments, the reference detector 100 receives x-rays directly from the high-energy x-ray source 250.

Figure 4A:
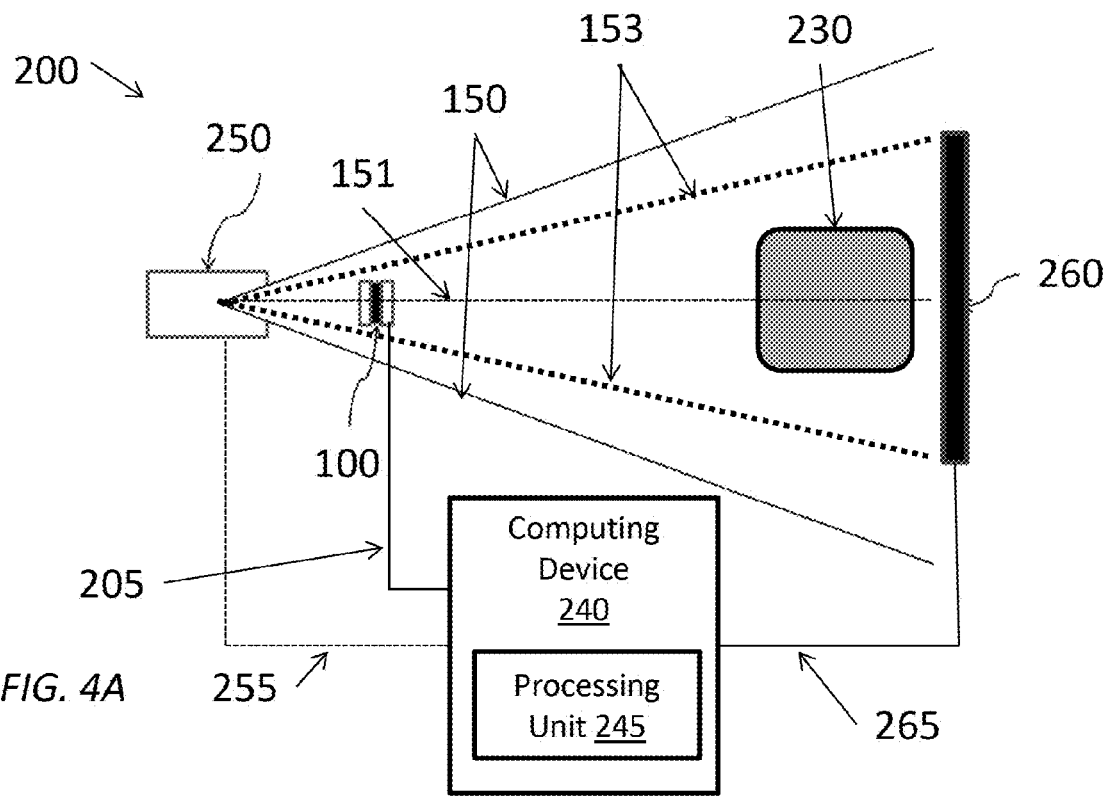

As shown in the example of FIG. 4A, the reference detector 100 can be positioned along the central axis 151 of the x-ray beam 150 and within the portion 153 of the x-ray beam 150 intercepted by the detector array 260. In this embodiment, the detector elements 101a-101n of the reference detector 100 can be exposed to a high flux of x-rays because the region between the origin of the beam of radiation (i.e., the high-energy x-ray source 250) and the first detector element 101a is free of solid objects. In this example, the output signal from each of the plurality of detector elements 160 can have a high signal-to-noise ratio. In embodiments such as that of shown in FIG. 4A, the distance between the reference detector 100 and the high-energy x-ray source 250 is less than the distance between the object 230 and the high-energy x-ray source 250. The placement of the reference detector 100 in this position can cause a portion of the x-ray beam 150 to be obstructed and lead to lower signal-to-noise ratio for segments of the detector array 260.

Figure 4B:
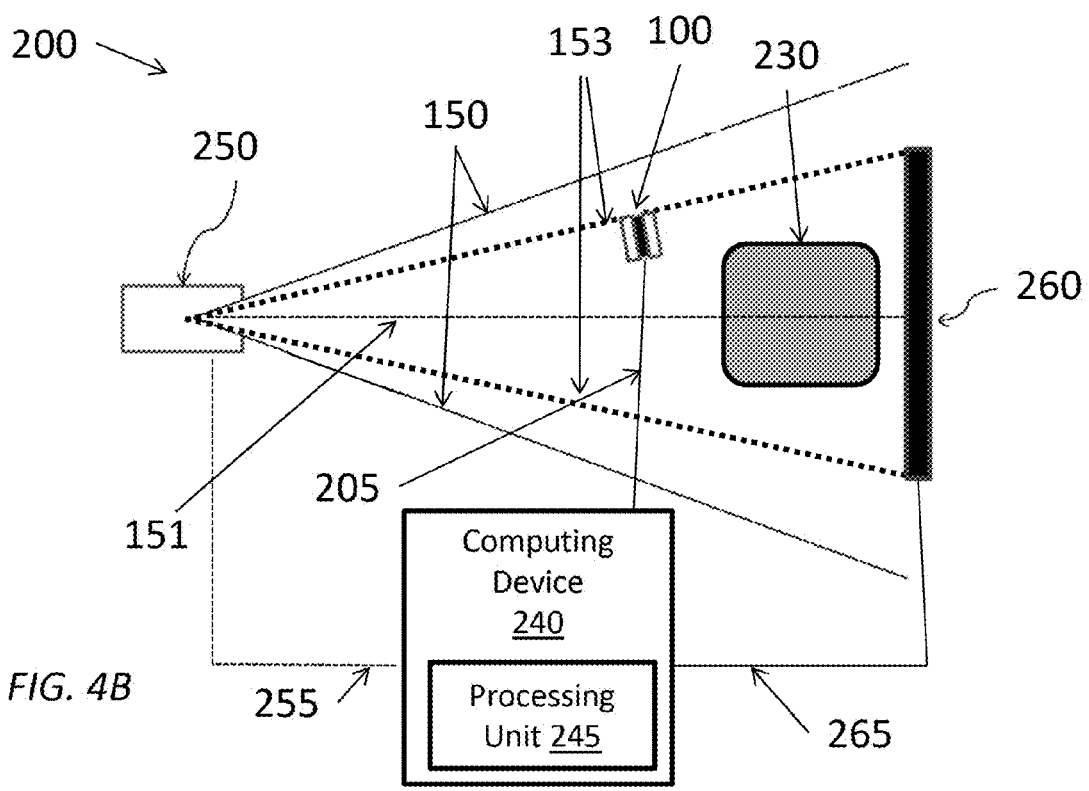

As illustrated in the example of FIG. 4B, the reference detector 100 may be positioned in a region of the x-ray beam 150 located away from the central axis 151 of the x-ray beam 150 yet still within the portion 153 of the x-ray beam 150 intercepted by the detector array 260. In some embodiments, the reference detector 100 can be positioned at the periphery of the x-ray beam 150 at a location offset from the central axis 151 of the x-ray beam 150 so as to not obstruct the path between the high-energy x-ray source 250 and the object 230. In some embodiments, at least a portion of the x-ray beam 150 from the high-energy x-ray source 250 can be broadened or uncollimated to direct that portion of the x-ray beam 150 to a reference detector 100 located at a position offset from the central axis 151. Placement of the reference detector 100 at a location away from the central axis 151 of the x-ray beam 150 may change the energy spectrum received at the reference detector 100. In some embodiments, the reference detector 100 or the signals or data received by computing device 240 from the reference detector 100 may be calibrated to reconcile or account for changes in the energy spectrum.

As illustrated in the example of FIG. 4C, the reference detector 100 may be located at or near the detector array 260. As shown in this figure, the distance between the reference detector 100 and the high-energy x-ray source 250 is greater than the distance between at least a portion of the object 230 and the high-energy x-ray source 250. In some embodiments, a portion of the detector array 260 can be configured to include the reference detector 100. For example, the reference detector 100 may be integrated directly into the detector array 260 or be mounted to a mount on a portion of the detector array 260. In some embodiments, the reference detector 100 can be positioned proximate to an end of the detector array 260. In an embodiment where the reference detector 100 is positioned proximate to an end of the detector array 260, the reference detector 100 can receive a portion of the x-ray beam 150 that did not interact with any portion of the object 230. In addition to the foregoing examples of FIGS. 4A-4D, it will be apparent to one of ordinary skill in the art that the reference detector 100 can be disposed at any position relative to the object 230 that allows the reference detector 100 to receive x-rays directly from the high-energy x-ray source 250.

As shown in the example of FIG. 4D, the reference detector 100 may be positioned in a region of the x-ray beam 150 located away from the central axis 151 of the x-ray beam 150 and outside of the portion 153 of the x-ray beam 150 intercepted by the detector array 260. By placing the reference detector 100 outside of the portion 153 of the x-ray beam 150 intercepted by the detector array 260, the reference detector 100 will not block any portion of the beam that passes through the object 230 or create a "shadow" on the detector array 260. Placement of the reference detector 100 at a location away from the central axis 151 of the x-ray beam 150 may change the energy spectrum received at the reference detector 100. In some embodiments, the reference detector 100 or the data received by computing device 240 from the reference detector 100 may be calibrated to reconcile or account for changes in the energy spectrum.

As shown in FIGS. 4A-4D, the example imaging system 200 can include a computing device 240 including a processing unit 245. The computing device 240 can be configured to exchange data, or instructions, or both data and instructions, with at least one of the other components of the imaging system 200 using communication links. For example, the computing device 240 including the processing unit 245 can be configured or programmed to use a feedback loop 255 to communicate with the high-energy x-ray source 250. The computing device 240 including the processing unit 245 can be configured or programmed to use a communication link 265 to communicate with the detector array 260. The computing device 240 including the processing unit 245 can be configured or programmed to use a communication link 205 to communicate with the reference detector 100. The communication links 205, 265 and feedback loop 255 can be wireless or can include one or more wires or cables.

The computing device 240 can use the communication links 205, 265 and feedback loop 255 to control the operation of or transmit or receive information from the reference detector 100, the high-energy x-ray source 250, and the detector array 265. In various examples, the computing device 240 including the processing unit 245 can be configured or programmed to receive object measurement data from the detector array 260 through the communication link 265. In some embodiments, the computing device 240 including the processing unit 245 can be configured or programmed to receive measurement data from the reference detector 100 through the communication link 205. In some embodiments, the computing device 240 including the processing unit 245 can control the operation of the high-energy x-ray source 250 through the feedback loop 255 including adjusting x-ray beam dose and energy.

In various examples, the computing device 240 including the processing unit 245 can be programmed to perform several operations. The processing unit 245 can receive object measurement data from the detector array 260 and measurements of an x-ray beam dose and the x-ray beam attenuation from the reference detector 100. In some embodiments, the measurements of an x-ray beam dose and the x-ray beam attenuation can include signals received from the plurality of detector elements 160 upon exposure to the x-ray beam 150. The processing unit 245 can compare object measurement data from the detector array 260 and measurements of x-ray beam dose or x-ray beam attenuation from the reference detector 100 to determine a dose correction factor, energy correction factor, or both. The processing unit 245 can correct the object measurement data from the detector array 260 by applying the dose correction factor, energy correction factor, or both. In an exemplary embodiment, the processing unit 245 can correct measurement data representing density of at least a portion of the object received from the detector array 260 by applying the dose correction factor derived from a comparison of the object measurement data to x-ray beam dose measurements from the reference detector 100 as described in greater detail below with reference to FIGS. 5-8B. In an exemplary embodiment, the processing unit 245 can correct measurement data representing effective atomic number of at least a portion of the object received from the detector array 260 by applying the energy correction factor derived from comparison of the object measurement data to x-ray beam attenuation measurements from the reference detector 100 as described in greater detail below with reference to FIGS. 9-10.

In an exemplary embodiment, the processing unit 245 can apply a dose correction factor or energy correction factor to the high-energy x-ray source 250 through the feedback loop 255 to adjust or stabilize the output of x-ray dose or energy.

Example computation of the beam dose correction factor and beam energy correction factor and correction of the object measurement data is now described. To correct fluctuations in the beam dose, a proportionality can be assumed between the relative yield change observed at the detector array 260 and at the reference detector 100:

$$\Delta Y/Y \approx -\Delta R_{air}/R_{air} \qquad (4)$$

where $R_{air}$ is the yield in the reference detector 100, $\Delta R_{air}$ is the change in the reference detector yield from the calibration value, Y is the measured yield in the detector array 260, and $\Delta Y$ is the correction to the detector array yield.

In some embodiments, corrections for fluctuations of the beam energy can be made after measuring an attenuation value in the reference detector 100. The change of attenuation in the reference detector 100 is used to correct the attenuation measurement in the detector array 260. The attenuation in the detector array 260 can be computed as follows:

$$y = -a \log(Y/Y_{air}) \qquad (5)$$

where $Y_{air}$ is the detector array yield without any object in the beam path. The attenuation in the reference detector 100 can be computed from the yield before ($R_{air}$) the attenuation and after (R) the attenuation, as follows:

$$r = -a \log(R/R_{air}) \qquad (6)$$

where values of R are computed from the one or more detector elements of the reference detector. In exemplary embodiments, values of R are computed from at least the first detector element 101a and the final detector element 101n. In some embodiments, there can be a linear relationship between the attenuation in the detector array 260 and the reference detector 100 due to the change in the beam energy spectrum, as follows:

$$\Delta y \approx -\alpha(y)\Delta r \qquad (7)$$

where $\alpha(y)$ is the slope of the correction. The term $\alpha(y)$ can depend on the configuration of the reference detector and can be obtained during an initial calibration.

In exemplary embodiments, the x-ray beam 150 passes through the first detector element 101a and the second detector element 101b of the reference detector 100. Variation in the signals generated by the first and second reference detectors in response to x-ray exposure can be manipulated to provide a measurement of the x-ray beam dose and an evaluation of the beam energy.

Figure 5:
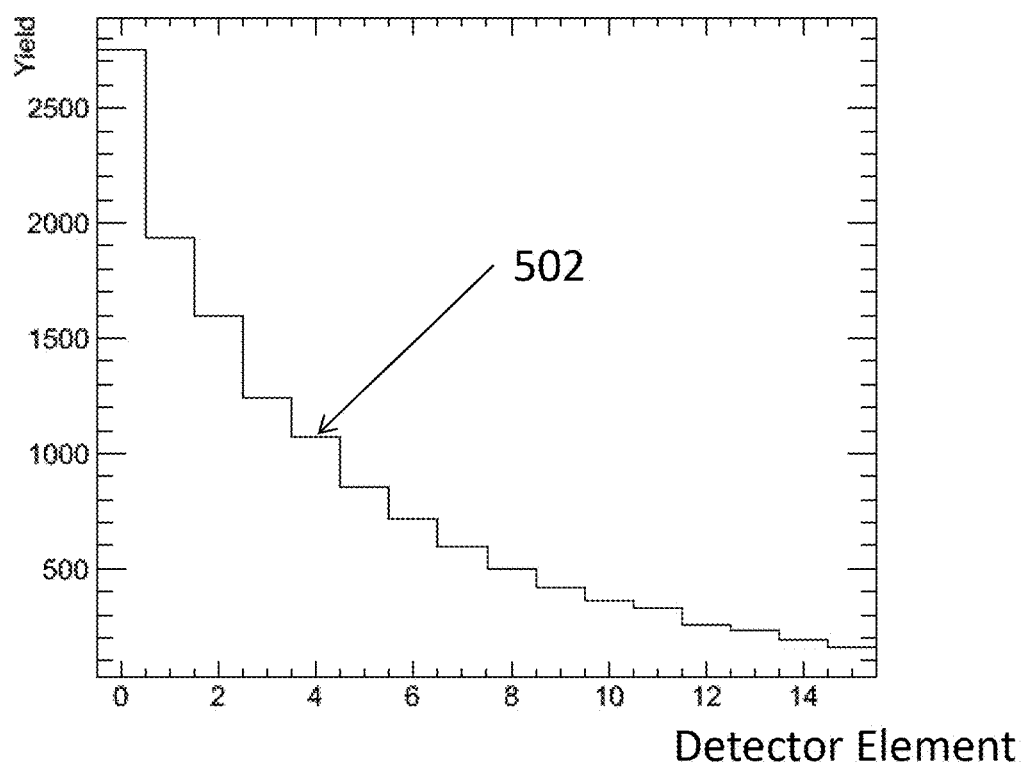
FIG. 5 illustrates an example yield for each stacked detector element in a reference detector, according to embodiments of the present disclosure.

A numerical example of attenuation of an x-ray beam 150 as it passes through the reference detector 100 is illustrated in FIG. 5. The data illustrated in FIG. 5 is based on an embodiment of the reference detector 100 having sixteen detector elements in a stacked relationship. The x-axis of FIG. 5 represents the detector element number, and the y-axis represents computed yield of signal per detector element in the plurality of detector elements. In this example, the x-ray beam 150 first passes through detector element 0 of reference detector 100" and then progressively through detector elements 1-15. The attenuation through the reference detector material is illustrated by the decreasing yield through the stacked detector elements of the reference detector 100". The yield profile curve 502 of FIG. 5 can be used to estimate the beam hardness, i.e., the endpoint energy of the x-ray spectrum. In the computational example of FIG. 5, the attenuation can be computed by Equation (6) using, for example, the first three detector elements ($R_{air}$) and the last three detector elements (R) of an example reference detector 100" through which the x-ray beam 150 passes. In other embodiments, the attenuation can be computed in relation with the exponential decay constant of the yield profile curve 502.

Figure 6:
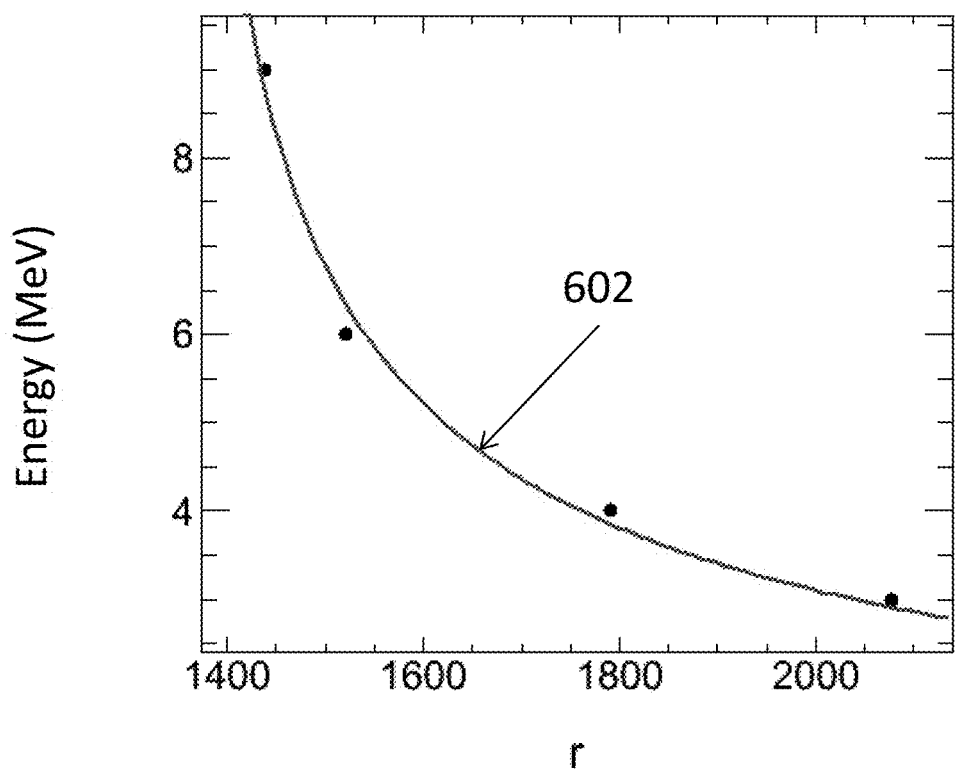
FIG. 6 illustrates an example log-attenuation ratio versus beam energy, according to embodiments of the present disclosure.

FIG. 6 illustrates an example plot 602 of the endpoint energy of the x-ray beam 150 as a function of the log-attenuation ratio calculated using Equation (6) with the value of a=656. The plot 602 shown in FIG. 6 can be used to determine the output energy of the x-ray beam 150 measured in the reference detector 100 by using the measured log-attenuation ratio. Once the output energy of the x-ray beam 150 has been determined, an energy correction factor can be calculated.

The relative error for the energy measurement can be expressed as:

$$\sigma_E/E (dE/dr)(r/E)\sigma_r/r \qquad (10)$$

where the scaling term $(dE/dr)(r/E)$ can be calculated by simulation.

Figure 7:
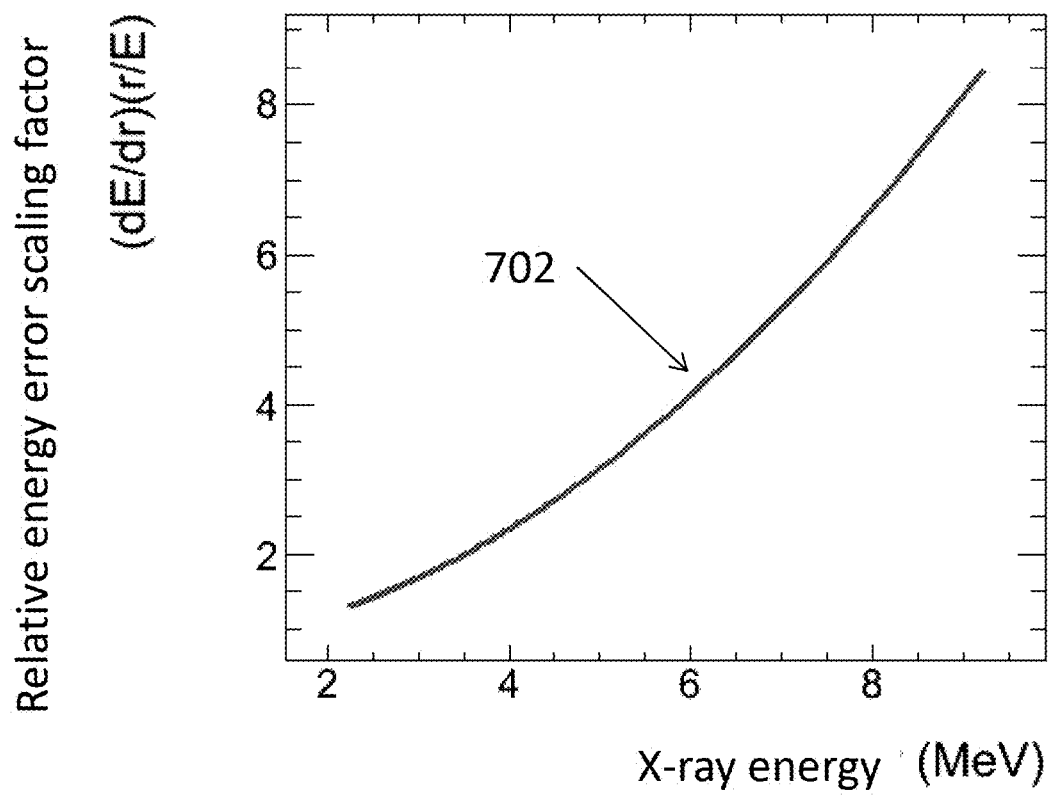
FIG. 7 illustrates an example scaling term for the relative energy error versus beam energy, according to embodiments of the present disclosure.

FIG. 7 shows an example plot 702 of the scaling term between the relative error in the beam energy and the attenuation measurements in the reference detector as a function of the x-ray energy in MeV. For example, in order to measure the energy of a 9 MeV beam with precision better than 1%, the measurement of attenuation in the reference detector 100 requires the collection of around 1 million x-rays per pulse. This can be achieved in a typical linear accelerator (linac) source near the beam exit slit.

Instead of using Equation (6) to compute the attenuation in the reference detector 100 as illustrated in FIG. 5, some embodiments of the present disclosure can enable extraction of the slope of an attenuation curve when the attenuation is measured at multiple depths. In various embodiments, the high-energy x-ray source 250 can produce a wide angular distribution of radiation that is collimated into a narrow, fan-shaped x-ray beam 150. If the reference detector 100 is placed in the main x-ray beam 150 that is used to scan objects, the reference detector 100 can obstruct a portion of the beam (usually a few degrees) and thereby increase the noise in the resulting radiographic image. In some embodiments, a portion of the x-ray beam 150 that is emitted at a high angle can be allowed to proceed without collimation, and the reference detector 100 can be positioned in this secondary beam outside of the main beam.

The reference detector 100 can be used to actively monitor the dose and energy of the high-energy x-ray source 250 for data quality and safety reasons. In addition to passive monitoring, the reference detector can be used in a feedback loop to improve the stability of the source in some embodiments. For example, the high-energy x-ray source 250 can rely on electron linear accelerators (linacs) that require adjustment of the RF frequency in order to keep the energy and the current of the electron beam constant. In an exemplary embodiment, the difference between a dose or energy of the x-ray beam 150 measured by the reference detector 100 and a desired dose or energy can be used to adjust the RF frequency of the electron linac via a feedback loop in order to keep the source stable as illustrated in FIGS. 4A-4D. For example, the computing device 240 including processing unit 245 can apply feedback to the high-energy x-ray source 250 using feedback loop 255. As a non-limiting example, the feedback can be used to correct an RF output frequency of the high-energy x-ray source, for example, a magnetron in order to counter thermally induced variation in the output frequency.

The utility and benefit of the example reference detector 100 was demonstrated in an example system as follows. The example system includes a gantry imaging system with a dual energy linac and the reference detector 100 including eight active detector elements 101*a*-101*h* made of CWO. A standard plastic plate including three metal wires formed of copper was used as the imaged object. The gantry speed was 0.4 m/s. The linac operated in interlaced mode at 200 pulses per second and 220 μGy/pulse and 100 μGy/pulse for 6 MeV and 4 MeV beam energies, respectively. The dose in the reference detector 100 was measured as the sum of signals from the eight detector elements 101*a*-101*h*, and the attenuation was measured as a ratio of the yields in the first two detectors 101*a*, 101*b* and the last two detectors 101*g*, 101*h*.

Figure 8A:
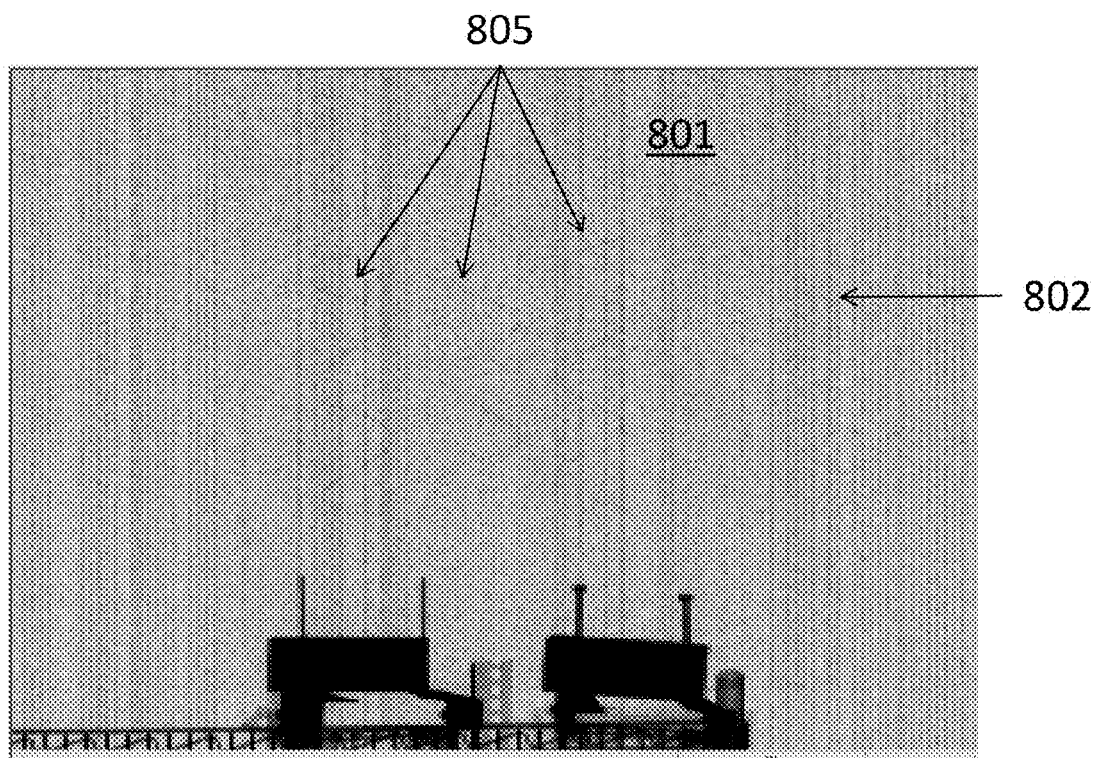
FIG. 8A shows an example image of an object obtained using an example x-ray radiography system without dose corrections, according to embodiments of the present disclosure.
Figure 8B:
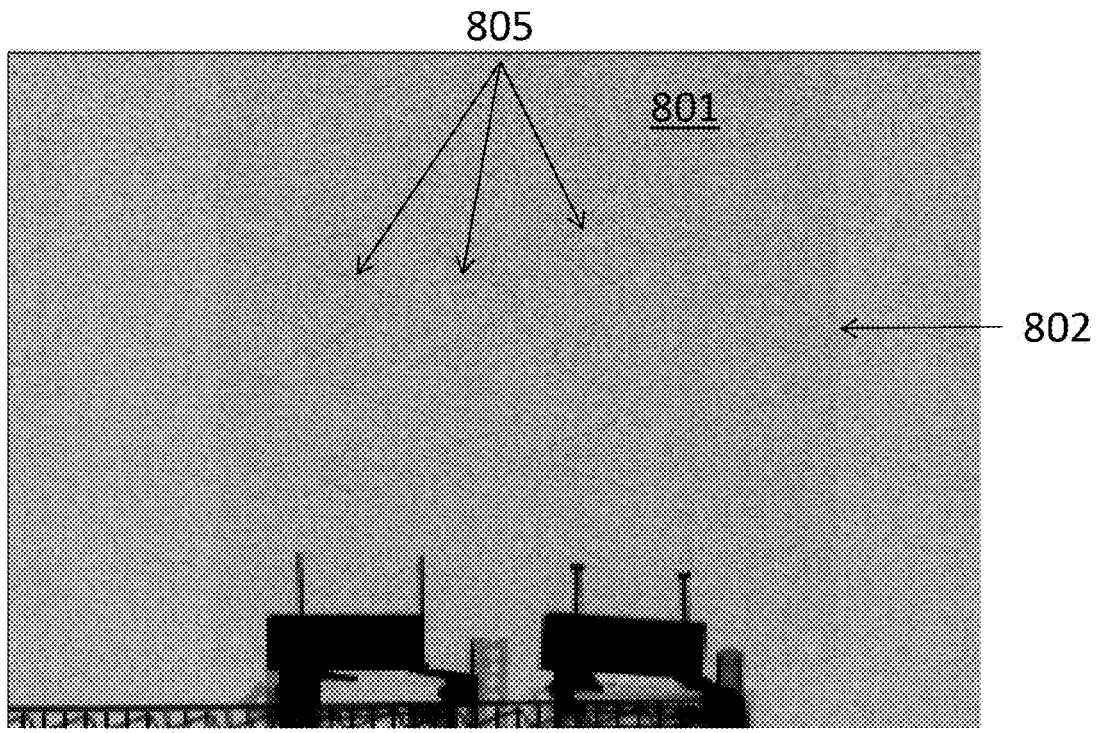
FIG. 8B shows an example image of an object obtained using an example x-ray radiography system with dose corrections, according to embodiments of the present disclosure.

The impact of dose corrections on the quality of the resulting image is shown in FIGS. 8A and 8B. A standard detection object including a plastic plate 801 and thin copper wires 805 was imaged using the above-described system. An image with no corrections is shown in FIG. 8A while FIG. 8B shows the same image area when corrections to fluctuations in x-ray beam dose have been implemented. As shown in FIG. 8A, the edges 802 of the plastic plate 801 are not visible, and the copper wires 805 can barely be seen. The edges 802 of the plastic plate 801 become more visible and the copper wires 805 are much clearer in the dose-corrected image of FIG. 8B as compared to the image of FIG. 8A.

Figure 9:
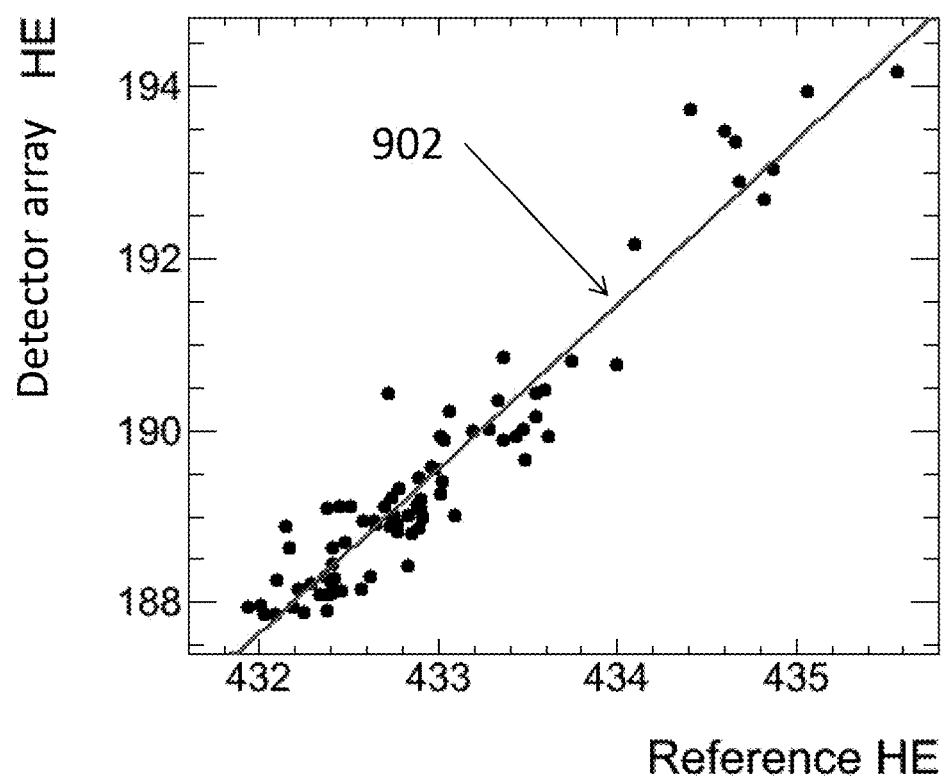
FIG. 9 illustrates example log-attenuation measurements during object imaging for a detector array and a reference detector, according to embodiments of the present disclosure.

To evaluate the benefit of corrections to x-ray beam energy measurements, the example system was used to perform multiple scans of a one-inch aluminum target as the object. The average attenuation was measured for each scan. FIG. 9 shows the log-attenuation in a 6 MeV beam for both the detector array 260 (i.e., for the x-ray beam that passed through the aluminum target) and the reference detector 100. The measures of attenuation are computed using Equation (5) and Equation (6) with the value a=656. The correlation between log-attenuation measurements in the target and the reference detector is also shown. Absent any x-ray beam source fluctuations, all measurements would fall on a single point. In a high energy x-ray source with energy fluctuations but no measurement error, measurement points would fall along a reference line 902. The measured distribution of points away from the reference line 902 illustrates the effect of both energy fluctuations and measurement error. The ratio between the values of log-attenuation at different energies can be used to measure the effective atomic number and, for example, to classify the object into a material group.

Figure 10:
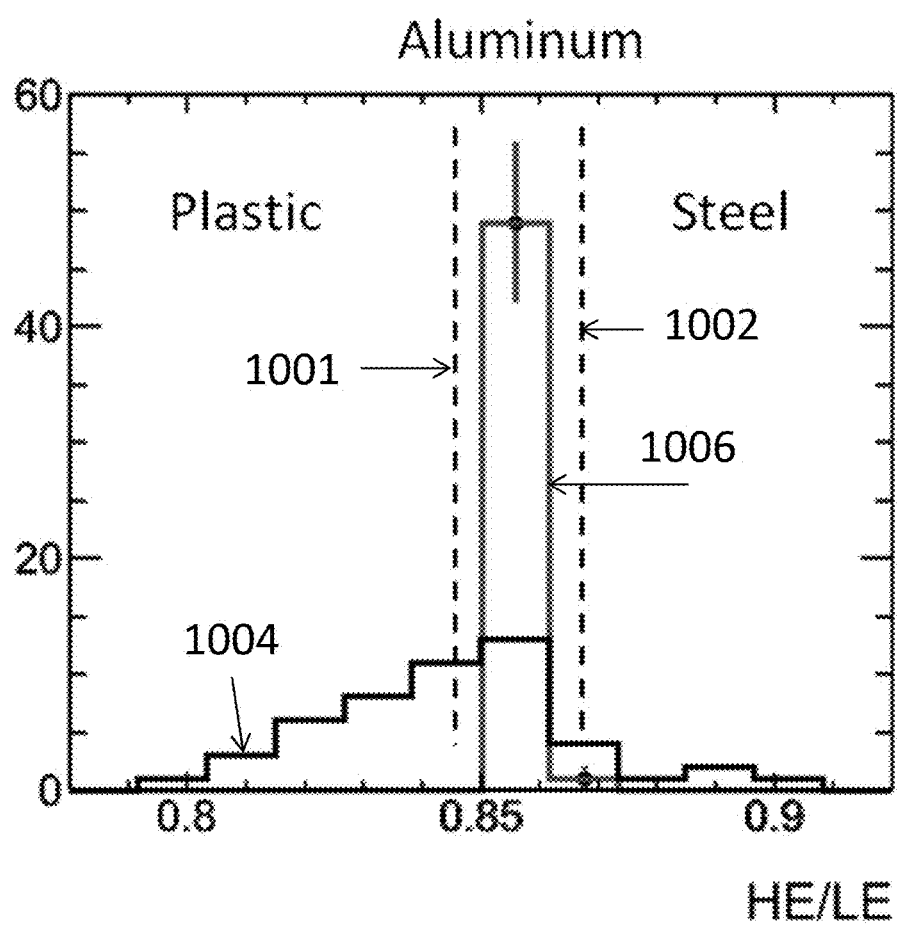
FIG. 10 illustrates the example distribution of the ratio of the high-energy measurement count to the low energy measurement count (HE/LE) parameter using uncorrected and corrected data obtained for an object using an example system, according to embodiments of the present disclosure.

FIG. 10 shows an example distribution of the ratio of the high-energy measurement count to the low energy measurement count (HE/LE) parameter for a one-inch aluminum target, before and after the application of corrections for both dose and energy fluctuations as taught herein. In FIG. 10, the vertical dashed lines 1001, 1002 separate different groups of materials. If the material has a HE/LE ratio that falls to the left of line 1001, the material is classified as a plastic. If the HE/LE ratio falls between lines 1001, 1002, the material is classified as aluminum. If the HE/LE ratio falls to the right of line 1002, the material is classified as steel. As shown in FIG. 10, the uncorrected distribution 1004 of HE/LE measurements for a single location in the object is broader than the width between the dashed vertical lines. This indicates that a number of these measurements may be miscategorized. In the corrected distribution 1006 of HE/LE measurements shown in FIG. 10, the distribution is dramatically narrower and is nearly all contained within the bounds of the category (i.e., within the vertical dashed lines 1001, 1002). By correcting for the energy and dose of the x-rays using a reference detector 100, the number of miscategorized measurements can be sharply reduced.

Figure 11:
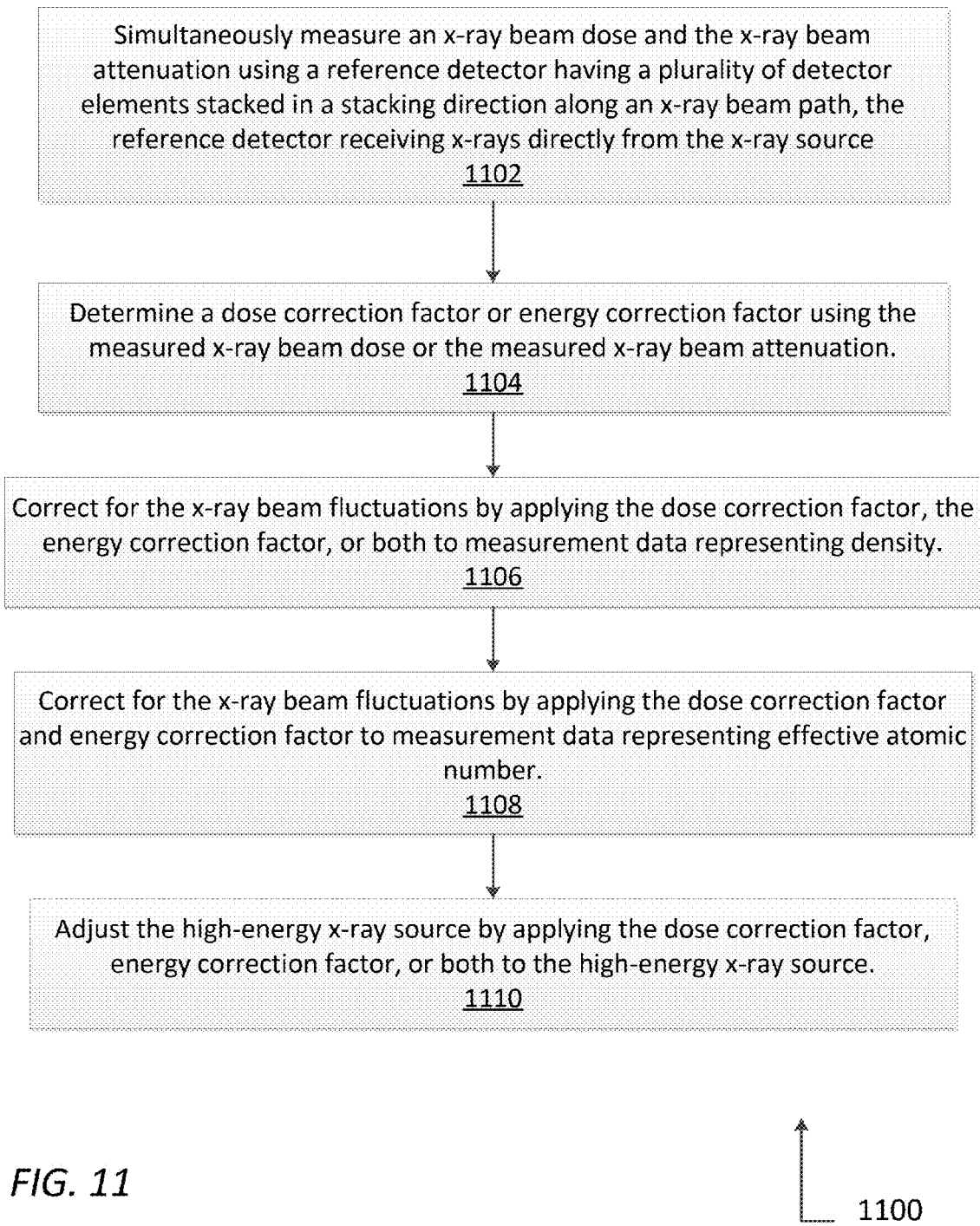
FIG. 11 illustrates an example method of correcting for x-ray beam fluctuations in a high-energy x-ray source, according to embodiments of the present disclosure.

FIG. 11 illustrates an example method 1100 of correcting for fluctuations in a beam of x-ray radiation from a high-energy x-ray source according to various embodiments of the present disclosure. The method includes the step 1102 of simultaneously measuring an x-ray beam dose and the x-ray beam attenuation using a reference detector 100 having a plurality of detector elements stacked one behind the other in a stacking direction along an x-ray beam path. The reference detector receives x-rays directly from the high-energy x-ray source. That is, the reference detector 100 has an unobstructed line of sight with an output of the x-ray source. In step 1104, a dose correction factor, energy correction factor, or both are determined using the measured x-ray beam dose or the measured x-ray beam attenuation, respectively. In step 1106, x-ray beam fluctuations are corrected by applying the dose correction factor, the energy correction factor, or both to measurement data representing density. In step 1108, x-ray beam fluctuations are corrected by applying the dose correction factor or energy correction factor to measurement data representing effective atomic number. In some embodiments, step 1110 is performed. In step 1110, the high-energy x-ray source is adjusted by applying the dose correction factor, energy correction factor, or both to the high-energy x-ray source.

The method 1100 uses the computing device 240 including the processing unit 245 to compare object measurement data received from the detector array 260 with a measured dose or attenuation value received from the reference detector 100, 100', 100", such as described above with reference to any of FIGS. 4A-4D.

Step 1106 can correct for the x-ray beam fluctuations by applying the dose correction factor, the energy correction factor, or both to measurement data representing density. This can be performed by using the computing device 240 including the processing unit 245 to correct x-ray beam fluctuations from the high-energy x-ray source 250 by applying the dose correction factor to reconstructed image data representing the density of a portion of an object 230 as described above with reference to FIGS. 4A-4D. Step 1108 can correct for the x-ray beam fluctuations by applying the dose correction factor and energy correction factor to measurement data representing effective atomic number. This can be performed by using the computing device 240 including the processing unit 245 to correct for the x-ray beam fluctuations from the high-energy x-ray source 250 by applying the dose correction factor and energy correction factor to reconstructed image data representing the effective atomic number of a portion of an object 230 as described above with reference to FIGS. 4A-4D.

In some embodiments that include feedback loop 255, step 1110 can adjust the high-energy x-ray beam source by applying the dose correction factor, energy correction factor, or both to the high-energy x-ray beam source. This can be performed by using the computing device 240 including the processing unit 245 to adjust the high-energy x-ray source 250 by applying the dose correction factor, energy correction factor, or both to the high-energy x-ray source 250 via the feedback loop 255 as described above with reference to FIGS. 4A-4D.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other embodiments, functions and advantages are also within the scope of the invention.

The invention claimed is:

1. An imaging system comprising:
    a high-energy x-ray source to irradiate at least a portion of an object with a beam of x-ray radiation;
    a detector array to detect object measurement data indicative of an interaction of x-rays with at least a portion of the object;
    a reference detector including a plurality of detector elements stacked in a stacking direction along an x-ray beam path to detect x-ray beam fluctuations in the high-energy x-ray source, the reference detector receiving x-rays directly from the high-energy x-ray source; and
    a processing unit having a central processing unit programmable to:
        receive object measurement data from the detector array and measurements of an x-ray beam dose and an x-ray beam attenuation from the reference detector;
        determine a dose correction factor or energy correction factor using the measured x-ray beam dose and the measured x-ray beam attenuation from the reference detector; and
        correct for x-ray beam fluctuations by applying the dose correction factor or energy correction factor to the object measurement data from the detector array.

2. The x-ray imaging system of claim 1, wherein the plurality of detector elements include:
    a first detector element having a first surface that faces the beam of x-ray radiation and a second surface opposite to the first surface, the first detector element producing a first signal on exposure to the beam of x-ray radiation; and
    a second detector element having a first surface and disposed behind the first detector element along the stacking direction such that the first surface of the second detector element faces the second surface of the first detector element, the second detector producing a second signal on exposure to portions of the beam of x-ray radiation that pass through the first detector element.

3. The x-ray imaging system of claim 1, wherein the dose correction factor and energy correction factor comprise data indicative of an energy or intensity for the beam of x-ray radiation.

4. The x-ray imaging system of claim 1, wherein the high-energy x-ray source produces x-rays having an energy of between 1 MeV and 20 MeV.

5. The x-ray imaging system of claim 2, wherein one or more additional detector elements are disposed between the first detector element and the second detector element.

6. The x-ray imaging system of claim 1, wherein one or more x-ray filters are disposed between at least two of the plurality of detector elements.

7. The x-ray imaging system of claim 6, wherein the x-ray filter comprises lead, tungsten, or a combination of both.

8. The x-ray imaging system of claim 1, wherein the plurality of detector elements comprise scintillator crystals.

9. The x-ray imaging system of claim 8, wherein the scintillator crystals comprise cadmium tungstate, lead tungstate, or cesium iodide.

10. The x-ray imaging system of claim 1, wherein the plurality of detector elements comprise at least one ionization chamber.

11. The x-ray imaging system of claim 1, wherein the distance between the reference detector and the high-energy x-ray source is less than the distance between the object and the high-energy x-ray source.

12. The x-ray imaging system of claim 1, wherein the distance between the reference detector and the high-energy x-ray source is greater than the distance between at least a portion of the object and the high-energy x-ray source.

13. The x-ray imaging system of claim 1, wherein the measurement data comprises data representing density or effective atomic number of at least a portion of the object.

14. The x-ray imaging system of claim 1, further comprising a feedback loop to adjust the x-ray beam source using the dose correction factor or energy correction factor.

15. The x-ray imaging system of claim 1, wherein the reference detector is disposed along a central axis of the beam of x-ray radiation.

16. The x-ray imaging system of claim 1, wherein the reference detector is disposed at a location offset from the central axis of the beam of x-ray radiation.

17. The x-ray imaging system of claim 16, wherein the reference detector is disposed outside of a portion of the beam of x-ray radiation intercepted by the detector array.

18. A method of correcting for fluctuations in a beam of x-ray radiation from a high-energy x-ray beam source, comprising:
    simultaneously measuring an x-ray beam dose and an x-ray beam attenuation using a reference detector having a plurality of detector elements stacked in a stacking direction along an x-ray beam path, the reference detector receiving x-rays directly from the high-energy x-ray source;
    determining a dose correction factor or energy correction factor using the measured x-ray beam dose or the measured x-ray beam attenuation;
    correcting for the x-ray beam fluctuations by applying the dose correction factor, the energy correction factor, or both to measurement data representing density; and
    correcting for the x-ray beam fluctuations by applying the dose correction factor and energy correction factor to measurement data representing effective atomic number.

19. The method of claim 18, further comprising adjusting the high-energy x-ray beam source by applying the dose correction factor, energy correction factor, or both to the high-energy x-ray beam source.

20. The method of claim 18, wherein the plurality of detector elements include:
    a first detector element having a first surface that faces the beam of x-ray radiation and a second surface opposite to the first surface, the first detector element producing a first signal on exposure to the beam of x-ray radiation; and
    a second detector element having a first surface and disposed behind the first detector element along the stacking direction such that the first surface of the second detector element faces the second surface of the first detector element, the second detector producing a second signal on exposure to portions of the beam of x-ray radiation that pass through the first detector element.

21. The method of claim 18, wherein simultaneously measuring the x-ray beam dose and the x-ray beam attenuation using the reference detector includes calculating the x-ray beam dose and the x-ray beam attenuation using measurement data from the plurality of detector elements.

22. The method of claim 18, wherein the dose correction factor and energy correction factor comprise data indicative of an energy or intensity for the beam of x-ray radiation.

23. The method of claim 18, wherein the high-energy x-ray source produces x-rays having an energy of between 1 MeV and 20 MeV.

24. The method of claim 20, wherein one or more additional detector elements are disposed between the first detector element and the second detector element.

25. The method of claim 18, wherein an x-ray filter is disposed between at least two of the plurality of detector elements.

26. The method of claim 25, wherein the x-ray filter comprises lead, tungsten, or a combination of both.

27. The method of claim 18, wherein the plurality of detector elements comprise at least one scintillator crystal.

28. The method of claim 27, wherein the scintillator crystal comprises cadmium tungstate, lead tungstate, or cesium iodide.

29. The method of claim 18, wherein the plurality of detector elements comprise at least one ionization chamber.

30. The method of claim 18, wherein the reference detector is disposed along a central axis of the beam of x-ray radiation.

31. The method of claim 18, wherein the reference detector is disposed at a location offset from a central axis of the beam of x-ray radiation.

32. The method of claim 31, wherein the reference detector is disposed outside of a portion of the beam of x-ray radiation intercepted by a detector array.

33. A reference detector, comprising:
a plurality of detector elements stacked in a stacking direction along an x-ray beam path to detect x-ray beam fluctuations wherein a first detector element in the plurality of detector elements receives x-rays directly from a high-energy x-ray source, and
wherein the stacking direction of the plurality of detector elements allows the reference detector to simultaneously detect a beam dose and a beam attenuation.

34. The reference detector of claim 33, wherein the plurality of detector elements include:
the first detector element having a first surface that faces the beam of x-ray radiation and a second surface opposite to the first surface, the first detector element producing a first signal on exposure to the beam of x-ray radiation; and
a second detector element having a first surface and disposed behind the first detector element along the stacking direction such that the first surface of the second detector element faces the second surface of the first detector element, the second detector producing a second signal on exposure to portions of the beam of x-ray radiation that pass through the first detector element.

35. The reference detector of claim 34, wherein the beam dose correlates to the first signal, the second signal, or a sum of the first signal and the second signal.

36. The reference detector of claim 33, wherein the beam attenuation correlates to an energy level of the beam of x-ray radiation.

37. The reference detector of claim 33, wherein the first detector element receives x-rays having an energy of between 1 MeV and 20 MeV.

38. The reference detector of claim 33, wherein an x-ray filter is disposed between at least two of the plurality of detector elements.

39. The reference detector of claim 38, wherein the x-ray filter comprises lead, tungsten, or a combination of both.

40. The reference detector of claim 33, wherein the plurality of detector elements comprise at least one scintillator crystal.

41. The reference detector of claim 40, wherein the scintillator crystal comprises cadmium tungstate, lead tungstate, or cesium iodide.

42. The reference detector of claim 33, wherein the plurality of detector elements comprise at least one ionization chamber.

43. The reference detector of claim 33, wherein the reference detector is disposed along a central axis of a beam of x-ray radiation.

44. The reference detector of claim 33, wherein the reference detector is disposed at a location offset from a central axis of a beam of x-ray radiation.

45. The reference detector of claim 44, wherein the reference detector is disposed outside of a portion of the beam of x-ray radiation intercepted by a detector array.

* * * * *